US00PP28820P3

(12) United States Plant Patent
Bernuetz et al.

(10) Patent No.: US PP28,820 P3
(45) Date of Patent: Dec. 26, 2017

(54) ***SCAEVOLA* PLANT NAMED 'BONSCA 1430'**

(50) Latin Name: *Scaevola aemula*
Varietal Denomination: Bonsca 1430

(71) Applicants: Andrew Bernuetz, Silverdale (AU); Mirza Mohammed Shoaib, Parramata (AU)

(72) Inventors: Andrew Bernuetz, Silverdale (AU); Mirza Mohammed Shoaib, Parramata (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 33 days.

(21) Appl. No.: 14/999,333

(22) Filed: Apr. 25, 2016

(65) Prior Publication Data

US 2017/0311527 P1 Oct. 26, 2017

(51) Int. Cl.
*A01H 5/02* (2006.01)

(52) U.S. Cl.
USPC ..... Plt./363

(58) Field of Classification Search
USPC ..... Plt./363
See application file for complete search history.

*Primary Examiner* — Keith Robinson
(74) *Attorney, Agent, or Firm* — C. A. Whealy

(57) ABSTRACT

A new and distinct cultivar of *Scaevola* plant named 'Bonsca 1430', characterized by its compact and spreading plant habit; freely branching habit; early and freely flowering habit; long flowering period; deep violet-colored flowers; and good container and garden performance.

1 Drawing Sheet

Botanical designation: *Scaevola aemula.*
Cultivar denomination: 'BONSCA 1430'.

BACKGROUND OF THE INVENTION

The present invention relates to a new and distinct cultivar of *Scaevola* plant, botanically known as *Scaevola aemula* and hereinafter referred to by the name 'Bonsca 1430'.

The new *Scaevola* plant is a product of a planned breeding program conducted by the Inventors in Yellow Rock, New South Wales, Australia. The objective of the breeding program is to create new compact, spreading and early-flowering *Scaevola* plants with numerous attractive flowers.

The new *Scaevola* plant originated from an open-pollination in Yellow Rock, New South Wales, Australia in March, 2013 of a proprietary selection of *Scaevola aemula* identified by the code number 13-12, not patented, as the female, or seed, parent with an unknown proprietary selection of *Scaevola aemula*, as the male, or pollen, parent. The new *Scaevola* plant was discovered and selected by the Inventors as a single flowering plant from within the progeny of the stated open-pollination in a controlled greenhouse environment in Yellow Rock, New South Wales, Australia on Mar. 4, 2014.

Asexual reproduction of the new *Scaevola* plant by vegetative tip cuttings in a controlled greenhouse environment in Yellow Rock, New South Wales, Australia since March, 2014 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca 1430'. These characteristics in combination distinguish 'Bonsca 1430' as a new and distinct *Scaevola* plant:

1. Compact and spreading plant habit.
2. Freely branching habit.
3. Early and freely flowering habit.
4. Long flowering period.
5. Deep violet-colored flowers.
6. Good container and garden performance.

Plants of the new *Scaevola* can be compared to plants of the female parent selection. Plants of the new *Scaevola* differ primarily from plants of the female parent selection in flowering habit as plants of the new *Scaevola* are more freely flowering than plants of the female parent selection.

Plants of the new *Scaevola* can be compared to plants of the *Scaevola aemula* 'Wesscaetob', disclosed in U.S. Plant Pat. No. 19,658. In side-by-side comparisons, plants of the new *Scaevola* differ from plants of the 'Wesscaetob' in the following characteristics:

1. Plants of the new *Scaevola* are more spreading than and not as mounding as plants of 'Wesscaetob'.
2. Plants of the new *Scaevola* flower earlier than plants of 'Wesscaetob'.
3. Plants of the new *Scaevola* and 'Wesscaetob' differ in flower petal color as plants of 'Wesscaetob' have violet blue-colored flower petals.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'Bonsca 1430' grown in a container.

The photograph at the bottom of the sheet is a close-up view of a typical flowering plant of 'Bonsca 1430'.

DETAILED BOTANICAL DESCRIPTION

The aforementioned photographs and following observations, measurements and values describe plants grown during the late summer in 20-cm containers in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were three months old when the photographs and the detailed description were taken. In the following description, color references are made to The Royal Horticultural Society Colour Chart, 2007 Edition, except where general terms of ordinary dictionary significance are used.

Botanical classification: *Scaevola aemula* 'Bonsca 1430'.

Parentage:

*Female, or seed, parent*.—Proprietary selection of *Scaevola aemula* identified as code number 13-12, not patented.

*Male or pollen parent*.—Unknown proprietary selection of *Scaevola aemula*, not patented.

Propagation:

*Type*.—By vegetative tip cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact and spreading plant habit; moderately vigorous growth habit.

*Branching habit*.—Freely branching habit with lateral branches potentially forming at every node; pinching enhances branching potential.

*Plant height*.—About 26.2 cm.

*Plant diameter* (*area of spread*).—About 75.1 cm.

Lateral branch description:

*Length*.—About 30 cm.

*Diameter*.—About 2.2 mm.

*Internode length*.—About 2.8 cm.

*Aspect*.—Upright to outwardly.

*Texture*.—Pubescent; rough.

*Color*.—Close to 143C.

Leaf description:

*Arrangement*.—Alternate, simple; sessile.

*Length*.—About 4.5 cm.

*Width*.—About 2.1 cm.

*Shape*.—Spatulate.

*Apex*.—Acute.

*Base*.—Attenuate.

*Margin*.—Sparsely serrate.

*Texture, upper and lower surfaces*.—Pubescent; rough.

*Venation pattern*.—Pinnate, reticulate.

*Color*.—Developing leaves, upper surface: Close to 137A. Developing leaves, lower surface: Close to 138A. Fully expanded leaves, upper surface: Close to N137B; venation, close to 144C. Fully expanded leaves, lower surface: Close to 138A; venation, close to 144A.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 2,000 flowers developing per plant during the flowering season.

*Flowering time*.—Early flowering habit, plants begin flowering after about four weeks after planting; long flower period, plants flower continuously from spring to autumn in Japan.

*Flower longevity*.—Flowers typically last about a week on the plant; flowers not persistent.

*Fragrance*.—Present, pleasant.

*Flower buds*.—Length: About 1.4 cm. Diameter: About 3.1 mm. Shape: Lenticular. Color: Close to 83C.

*Flowers*.—Diameter: About 1.3 cm by 2.3 cm. Depth: About 8.4 mm. Throat diameter: About 3.6 mm. Tube length: About 1 cm. Tube diameter, distally: About 2.8 mm. Tube diameter, proximally: About 2 mm.

*Petals*.—Quantity per flower: Five, fused at base. Length, beyond tube: About 1.1 cm. Width, beyond tube: About 4.2 mm. Shape: Narrowly elliptic. Apex: Cuspidate. Margin: Entire; weakly undulate. Texture, upper and lower surfaces: Smooth, glabrous. Texture, throat and tube: Pubescent. Color: When opening, upper surface: Close to 83A. When opening, lower surface: Close to N81A; midrib, close to 196D. Fully opened, upper surface: Close to 83A; towards the throat, close to 155A; color does not change with development. Fully opened, lower surface: Close to N81A; midrib, close to 196D. Throat, distally: Close to 1A; venation, close to 83A. Throat, proximally: Close to 1B; venation, close to 83A. Tube: Close to 150C; venation, close to 79C.

*Sepals*.—Quantity per flower: Two. Length: About 3.2 mm. Width: About 1.5 mm. Shape: Lanceolate. Apex: Acute. Base: Fused. Margin: Entire. Texture, upper and lower surfaces: Pubescent. Color, upper and lower surfaces: Distally, close to 137B; proximally, close to 144C.

*Reproductive organs*.—Androecium: Stamen quantity per flower: Five. Filament length: About 3.4 mm. Filament color: Close to 145C; distally, strongly tinged with close to N77B. Anther size: About 1.6 mm by 0.8 mm. Anther shape: Ellipsoidal. Anther color: Close to 161A. Pollen: Scarce. Pollen color:

Close to 4C. Gynoecium: Pistil quantity per flower: One. Pistil length: About 1.1 cm. Style color: Close to 145C tinged with close to 71A. Stigma color: Close to 199A. Ovary color: Close to 144C.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen & pest resistance: Plants of the new *Scaevola* have not been shown to be resistant to pathogens and pests common to *Scaevola* plants.

It is claimed:

1. A new and distinct *Scaevola* plant named 'Bonsca 1430' as illustrated and described.

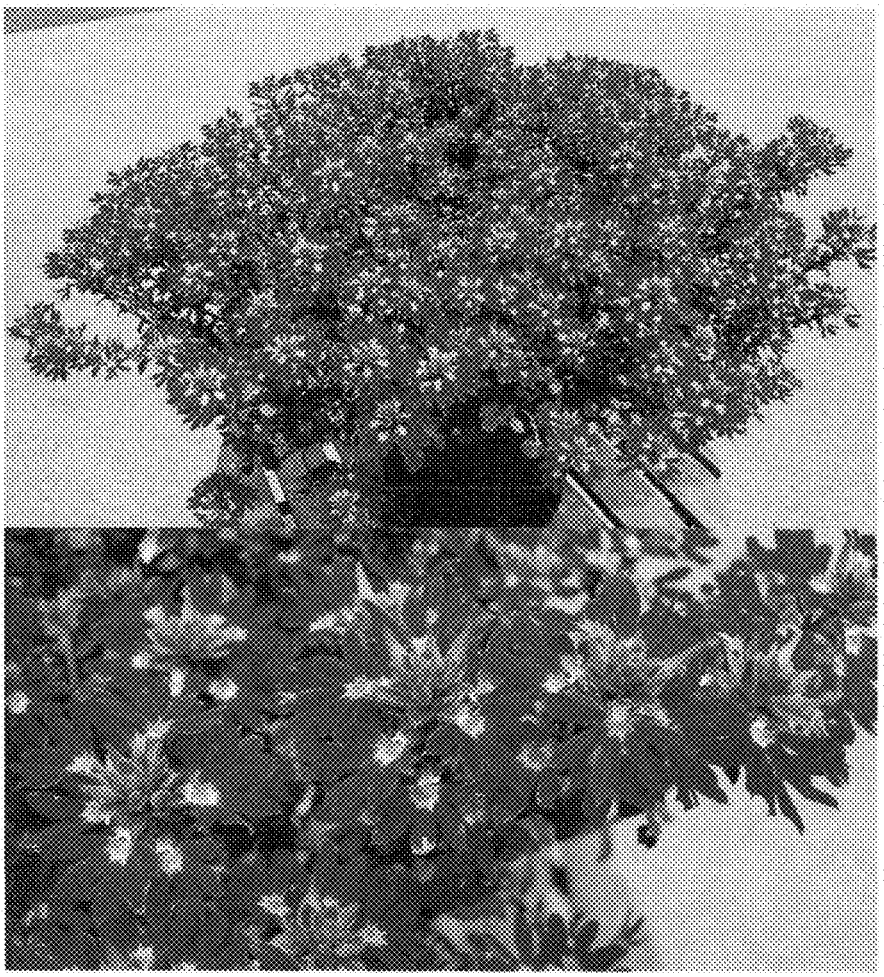

* * * * *